(12) United States Patent
Lim et al.

(10) Patent No.: US 12,266,836 B2
(45) Date of Patent: Apr. 1, 2025

(54) TRANSPARENT MICROBIAL ENERGY DEVICE

(71) Applicant: Industry-Academic Cooperation Foundation, Dankook University, Yongin-si (KR)

(72) Inventors: Eun Ju Lim, Yongin-si (KR); Young Seok Song, Seoul (KR)

(73) Assignee: Industry-Academic Cooperation Foundation, Dankook University, Yongin-si (KR)

( * ) Notice: Subject to any disclaimer, the term of this patent is extended or adjusted under 35 U.S.C. 154(b) by 597 days.

(21) Appl. No.: 17/474,013

(22) Filed: Sep. 13, 2021

(65) Prior Publication Data

US 2022/0209273 A1 Jun. 30, 2022

(30) Foreign Application Priority Data

Dec. 31, 2020 (KR) .................. 10-2020-0189521
Dec. 31, 2020 (KR) .................. 10-2020-0189523
Aug. 31, 2021 (KR) .................. 10-2021-0115667

(51) Int. Cl.
*H01M 8/16* (2006.01)
*C12N 1/12* (2006.01)
*C12N 1/20* (2006.01)
*C12N 11/04* (2006.01)
*H01M 4/86* (2006.01)
(Continued)

(52) U.S. Cl.
CPC .............. *H01M 8/16* (2013.01); *C12N 1/12* (2013.01); *C12N 1/20* (2013.01); *C12N 11/04* (2013.01); *H01M 4/8657* (2013.01); *H01M 4/8673* (2013.01); *H01M 4/8825* (2013.01); *C12N 2513/00* (2013.01); *C12N 2529/10* (2013.01);
(Continued)

(58) Field of Classification Search
CPC ........ H01M 8/16; H01M 8/22; H01M 8/1004; H01M 4/8657; H01M 4/8673; H01M 4/8825; C12N 1/12; C12N 1/20; C12N 11/04; C12N 2513/00; C12N 2529/10; C12N 2533/12; C12N 2533/30; C12R 2001/89
See application file for complete search history.

(56) References Cited

U.S. PATENT DOCUMENTS

2017/0077541 A1 3/2017 Togo et al.

FOREIGN PATENT DOCUMENTS

JP 2013-501315 A 1/2013
JP 5598883 B2 10/2014
(Continued)

OTHER PUBLICATIONS (computer-generated translatio of KR 20170142124) Song et al., "Photosynthetic Cell Based on Graphene and Cabon Nanotube and Manufacturing Method Thereof", Dec. 2017.*

*Primary Examiner* — Raymond Alejandro
(74) *Attorney, Agent, or Firm* — Park, Kim & Suh, LLC

(57) ABSTRACT

A transparent microbial energy device includes a first transparent electrode, a first hydrogel layer disposed on the first transparent electrode, an ion conductive polymer electrolyte membrane disposed on the first hydrogel layer, a second hydrogel layer disclosed on the ion conductive polymer electrolyte membrane, and a second transparent electrode disposed on the second hydrogel layer. The first hydrogel layer includes algal cells, and the second hydrogel layer includes potassium ferricyanide.

6 Claims, 2 Drawing Sheets

(51) Int. Cl.
*H01M 4/88* (2006.01)
*C12R 1/89* (2006.01)
(52) U.S. Cl.
CPC ...... *C12N 2533/12* (2013.01); *C12N 2533/30* (2013.01); *C12R 2001/89* (2021.05)

(56) References Cited

FOREIGN PATENT DOCUMENTS

| | | | | |
|---|---|---|---|---|
| JP | 6342969 B2 | 6/2018 | | |
| KR | 10-1312269 B1 | 9/2013 | | |
| KR | 10-1352551 B1 | 2/2014 | | |
| KR | 10-1694576 B1 | 1/2017 | | |
| KR | 10-1790840 B1 | 10/2017 | | |
| KR | 20170142124 A | * 12/2017 | ............. | H01M 8/16 |
| KR | 10-1899083 B1 | 9/2018 | | |
| KR | 10-2019-0033126 A | 3/2019 | | |
| KR | 10-1957023 B1 | 3/2019 | | |
| KR | 10-2020-0112487 A | 10/2020 | | |
| KR | 10-2020-0121181 A | 10/2020 | | |
| KR | 10-2020-0138147 A | 12/2020 | | |
| WO | WO-2009146143 A2 | * 12/2009 | ............. | B03C 5/005 |

* cited by examiner

TRANSPARENT MICROBIAL ENERGY DEVICE

CROSS-REFERENCE TO RELATED APPLICATIONS

A claim for priority under 35 U.S.C. § 119 is made to Korean Patent Application Nos. 10-2020-0189521 filed on Dec. 31, 2020, 10-2020-0189523 filed on Dec. 31, 2020, and 10-2021-0115667 filed on Aug. 31, 2021, in the Korean Intellectual Property Office, the entire contents of which are hereby incorporated by reference.

BACKGROUND

Embodiments of the inventive concept described herein relate to a transparent microbial energy device and a manufacturing method thereof.

Most of fossil fuels used produce carbon dioxide and accelerate global warming and have environment problems. Accordingly, various energy sources to replace the fossil fuels are being studied. Among them, research to convert solar energy into electrical energy, such as a solar cell, is being actively conducted. The solar energy is an energy source that may be used almost infinitely on Earth, but in converting the solar energy into electric energy, there are still insufficient points in terms of efficiency or cost, thereby not being widely used.

Meanwhile, a microbial fuel cell (MFC) using electrons generated from energy metabolism of microorganisms, which uses electrons generated from the energy metabolism of the microorganisms. During a process in which the microorganisms decompose organic matter to produce ATP, electrons and hydrogen protons are generated, which the MFC uses. The electrons generated from the microorganisms are transferred to an anode of the microbial fuel cell, and the hydrogen protons generated from the microorganisms pass through a semi-permeable material that isolates ions of the microbial fuel cell and diffuse to the cathode. The diffused hydrogen protons are finally reduced to water by reacting with the electrons and dissolved oxygen present in the cathode, and a flow of the electrons generated in the process produces electricity by allowing a potential difference to be formed between the cathode and the anode.

Conventionally, the technology for the microbial fuel cell has been applied for and published in a number of other applications than the Republic of Korea Application No. 10-2013-0048692 "Microorganism fuel cell and manufacturing method thereof". However, most microbial fuel cells do not have high power production efficiency and are difficult to maintain for a long period of time considering a survival period of the microorganisms.

Therefore, it is necessary to develop a microbial cell that use the solar energy, and thus produces efficiently electricity and improves survival rate of microorganisms to be used permanently.

SUMMARY

Embodiments of the inventive concept provide a transparent microbial energy device capable of efficiently capturing hydrogen generated from microorganisms using potassium ferricyanide and securing transparency by thinly coating a hydrogel layer containing an algal cell to a thickness of a single cell layer, and a method of manufacturing the same.

Meanwhile, the technical problems to be achieved in the inventive concept are not limited to the technical problems mentioned above, and another technical problem not mentioned will be clearly understood by those of ordinary skill in the art to which the inventive concept belongs from the following description.

According to an exemplary embodiment, a method of manufacturing a transparent microbial energy device includes disposing a first transparent electrode, disposing a first hydrogel layer including an algal cell on the first transparent electrode, disposing a Nafion™ layer on the first hydrogel layer, disposing a second hydrogel layer including potassium ferricyanide on the Nafion™ layer, and disposing a second transparent electrode on the second hydrogel layer.

In addition, the first hydrogel layer may have a single cell layer structure and may have a thickness of 8 to 12 µm.

In addition, the first hydrogel layer may include dispersed glass beads and a conductive material.

In addition, the glass beads may be included at 0.1 wt % to 5 wt % with respect to the total weight of hydrogel of the first hydrogel layer.

In addition, the glass bead may have a length of 8 to 12 µm.

In addition, the first hydrogel layer may be disposed by one of a coating method of bar coating, knife coating, and slot coating.

In addition, the second transparent electrode may further include a graphene monolayer.

In addition, the second hydrogel layer may collect hydrogen ions that diffuse through the Nafion™ layer.

According to an exemplary embodiment, transparent microbial energy device includes a first transparent electrode, a first hydrogel layer disposed on the first transparent electrode and including an algal cell, a Nafion™ layer disposed on the first hydrogel layer, a second hydrogel layer disposed on the Nafion™ layer and including potassium ferricyanide, and a second transparent electrode disposed on the second hydrogel layer.

In addition, the first hydrogel layer may have a single cell layer structure and may have a thickness of 8 to 12 µm.

In addition, the first hydrogel layer may include a plurality of dispersed glass beads and a conductive material.

In addition, the glass beads may be included at 0.1 wt % to 5 wt % with respect to the total weight of hydrogel of the first hydrogel layer.

In addition, the glass bead may have a length of 8 to 12 µm.

In addition, the second transparent electrode may further include a graphene monolayer.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Figure 1:
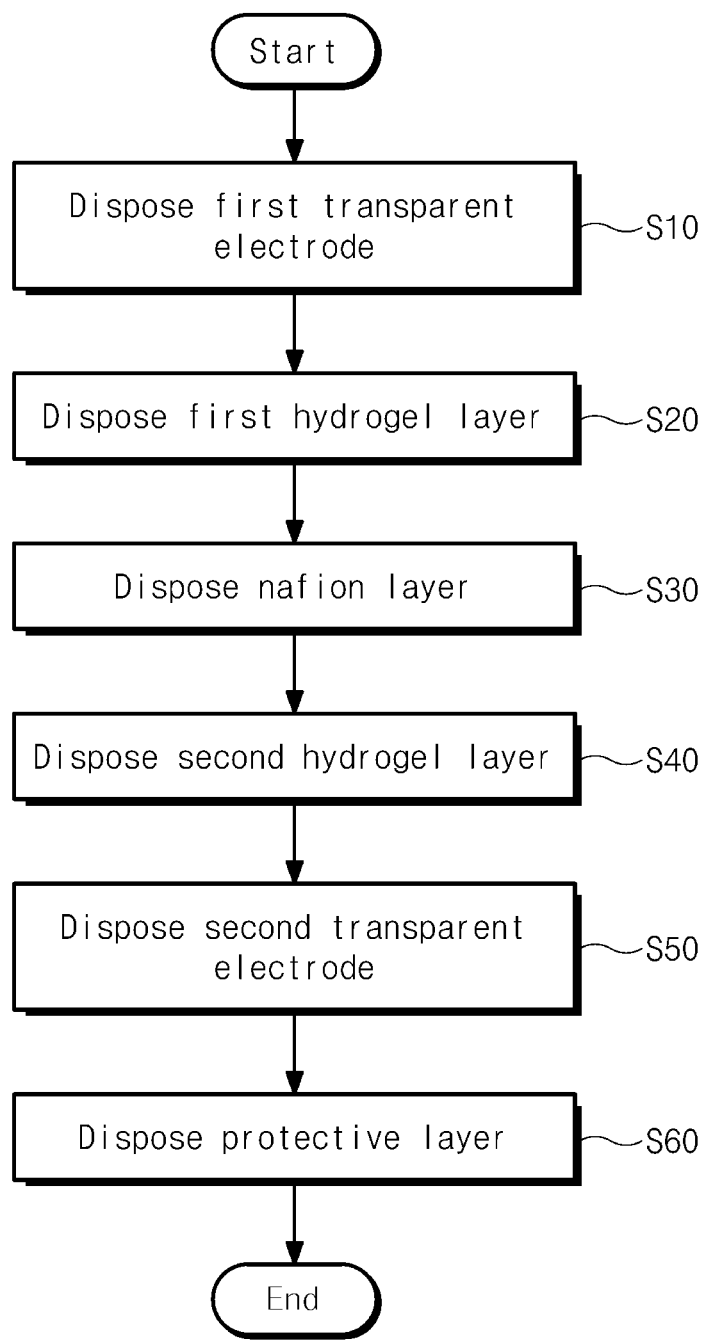
FIG. 1 is a flowchart illustrating a method of manufacturing a transparent microbial energy device according to an embodiment of the inventive concept.

Hereinafter, an embodiment of the inventive concept will be described in more detail with reference to the accompanying drawings. Embodiments of the inventive concept may be modified in various forms, and the scope of the inventive concept should not be construed as being limited to the following embodiments. This embodiment is provided to more completely explain the inventive concept to those of ordinary skill in the art. Accordingly, the shapes of elements in the drawings are exaggerated to emphasize a clearer description.

The configuration of the inventive concept for clarifying the solution of the problem to be solved by the inventive concept will be described in detail with reference to the accompanying drawings based on a preferred embodiment of the inventive concept, but in giving reference numerals to the components of the drawings, the same reference numbers are assigned to the same components even when they are on different drawings, and it is noted in advance that components of other drawings can be cited when necessary in the description of the drawings.

Figure 2:
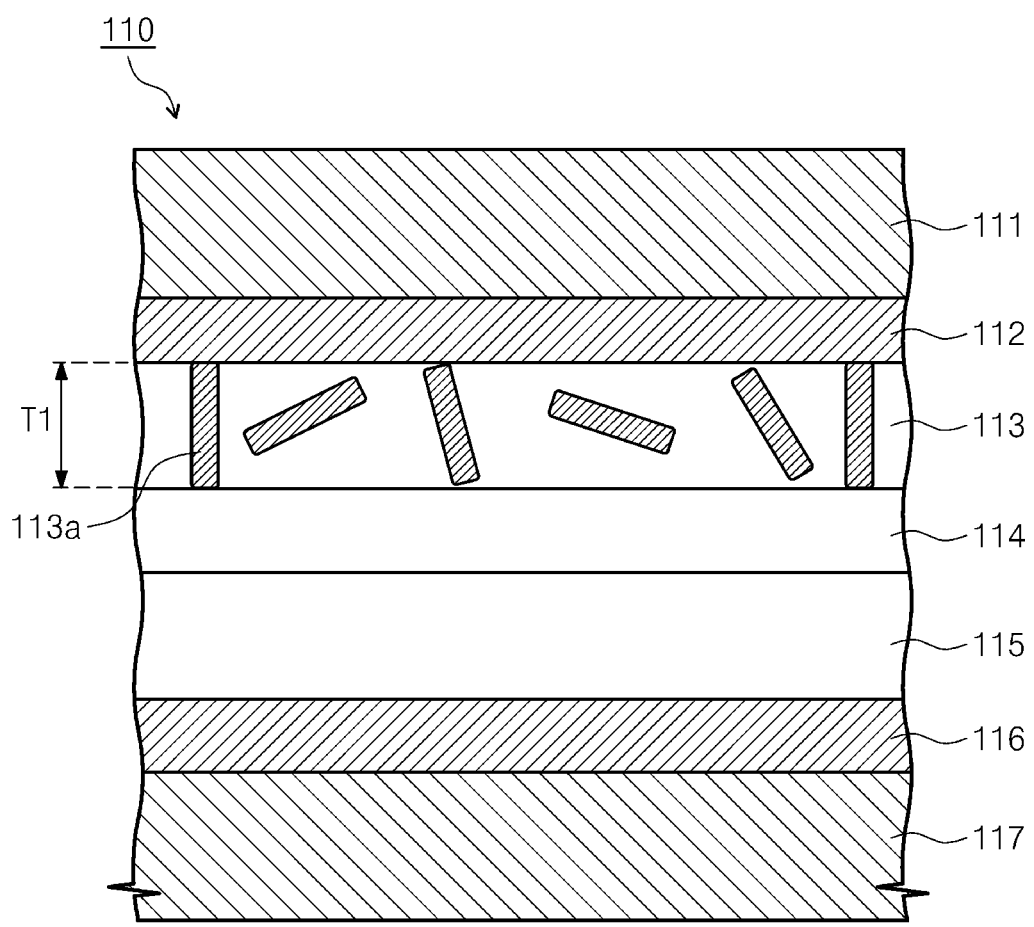
FIG. 2 is a view for illustrating a transparent microbial energy device manufactured by a method of manufacturing a transparent microbial energy device according to an embodiment of the inventive concept.

FIG. 1 is a flowchart illustrating a method of manufacturing a transparent microbial energy device according to an embodiment of the inventive concept, and FIG. 2 is a view for illustrating a transparent microbial energy device manufactured by a method of manufacturing a transparent microbial energy device according to an embodiment of the inventive concept.

A transparent microbial energy device according to an embodiment of the inventive concept includes a layer made of a hydrogel including an algal cell and a conductive material, and the algal cell is a cell capable of maintaining its viability while performing photosynthesis and when irradiated with light, photosynthesis occurs, and electrons are generated. The generated electrons are transferred to a second electrode through the conductive material, and the transparent microbial energy device is an organic semiconductor device using this principle.

The organic semiconductor device of the inventive concept is environmentally friendly because it does not require the use of a toxic electron transporter by using the algal cell that is capable of collecting electrons, easily.

In addition, the transparent microbial energy device of the inventive concept may easily supply energy to cells by using a hydrogel liquid, thereby increasing efficiency of the organic semiconductor device.

Referring to FIGS. 1 and 2, a method of manufacturing a transparent microbial energy device according to an embodiment of the inventive concept may include disposing a first transparent electrode in S10, disposing a first hydrogel layer in S20, disposing a Nafion™ layer in S30, disposing a second hydrogel layer in S40, disposing a second transparent electrode in S50, and disposing a protective layer in S60.

Referring to FIG. 2, the transparent microbial energy device manufactured includes a first protective layer 111, a first transparent electrode 112, a first hydrogel layer 113, a Nafion™ layer 114, a second hydrogel layer 115, a second transparent electrode 116, and a second protective layer 117.

In the disposing of the first transparent electrode of S10, the first transparent electrode 112 is disposed on the first protective layer 111.

The first protective layer 111 is configured in pairs with a second protective layer 117 to be described later and protects the transparent microbial energy device 100 from external impact. Meanwhile, the first protective layer 111 is preferably formed of a transparent layer such that light can be incident therein.

The first transparent electrode 112 may include an ITO electrode used as a transparent electrode, and an electrode that is capable of being applied transparently and is not transparent may be applied as the transparent electrode. Pt or Au which is formed as a thin film through vacuum deposition to secure transparency may be used as the transparent electrode. These materials are electrochemically stable materials, and in particular, Pt is a very electrochemically stable material, and therefore Pt or Au may be a preferable application example.

In the disposing of the first hydrogel layer of S20, the first hydrogel layer 113 is disposed on the first transparent electrode 112 as a single cell layer.

In addition, the first hydrogel layer 113 may include an algal cell and a plurality of dispersed glass beads 113a, and a conductive material.

First, the term 'hydrogel' used in the inventive concept is also called aquagel, refers to a hydrophilic gel in which a three-dimensional network structure, and exhibits elasticity almost similar to that of a natural tissue because of its moisture content.

The hydrogel that is capable of being included in the inventive concept may be used without limitation as long as it may provide a cell survival environment, and may be used with, for example, a smart gel that detects pH, temperature, or metabolite concentration, silicone hydrogel, polyacrylamide hydrogel, agarose hydrogel, methylcellulose hydrogel, polyvinyl alcohol hydrogel, sodium polyacrylate hydrogel, acrylate hydrogel, chondroitin hydrogel, glucosamine hydrogel, glycosaminoglycan hydrogel, fibrin hydrogel, fibrinogen hydrogel, thrombin hydrogel, hyaluronic acid hydrogel, collagen hydrogel, or the like, but is not necessarily limited thereto.

In addition, as used herein, the term 'algae cell' refers to an organism that lives in water and performs photosynthesis like plants in a comprehensive way, and includes Chlorophyte, Phaeophyceae, Rhodophyte, Cyanophyta, Bacillariophycea, Dinophyta, Or Haptophyta. Among them, cyanobacteria, also called blue-green algae plants and cyanobacteria, may belong to a primitive photosynthetic organism, and may belong to various species, such as a single-celled type, a group of single cells forming a colony, and a multicellular filamentous type, and includes, for example, Anabeana, Nostoc, Microcolous, Schizothrix, Synechococcus, and the like.

In various respects, Cyanophyta is located between bacteria and higher plants, and unlike higher plants, they are made of prokaryotic cells like bacteria, but are similar to green plants in terms of nutritional intake. Green algae are all green algae among protists and have various types such as unicellular, multicellular, and noncellular polynuclear. Most of green algae live in freshwater, but some live in seawater, and contain photosynthetic pigments such as chlorophylls a and b, carotene and xanthophylls. Green algae may include chlorella, desmid, green laver, spirogyra, and the like.

According to an embodiment, the algal cells may be at least one selected from the group consisting of Anabeana, Nostoc, Microcolous, Schizothrix, Synechococcus, Chlorella, desmid, green laver, and spirogyra.

Meanwhile, the algal cells may be chlorophyte or Cyanophyta. Chlorophyte or Cyanophyta commonly found in rivers and seas, have strong fertility, and may generate electrons and hydrogen ions through photosynthesis. Therefore, chlorophyte or Cyanophyta is suitable for use in a photosynthetic battery because the inventive concept has a configuration capable of capturing electrons and hydrogen ions therefrom.

In particular, in the case of chlorophyte, electrons are on the outside of the cell, and it may be easier to collect the electrons.

In the first hydrogel layer 113, the number of algal cells is included in $1\times10^6$ to $1\times10^{10}$, preferably $1\times10^7$ to $1\times10^9$, per 1 mL of the hydrogel.

When the number of algae cells in the first hydrogel layer 113 is less than $1\times10^6$, the amount of photosynthesis is insufficient not to be used as a driving energy source for an organic semiconductor device. When the number of algae cells in the first hydrogel layer 113 exceeds $1\times10^{10}$, turbidity of the hydrogel increases, survival of chlorophyte becomes difficult. and photosynthetic reactions do not occur.

Meanwhile, a thickness T1 of the first hydrogel layer 113 is preferably 8 μm to 12 μm.

Here, when the thickness T1 of the first hydrogel layer 113 is less than 8 μm, it is difficult to expect a process of generating electrons and hydrogen ions by the dispersed algal cells. When the thickness T1 of the first hydrogel layer 113 is more than 12 μm, the first hydrogel layer 113 gradually becomes opaque by the dispersed algal cells, and efficiency of generating the electrons and hydrogen ions is reduced by preventing light from entering.

The conductive material included in the first hydrogel layer 113 serves as an intermediate medium for transferring electrons generated through photosynthesis of the algal cells to the second transparent electrode 116.

In the inventive concept, the conductive material is not particularly limited in its kind, but preferably has a rod-shaped or plate-shaped structure to advantageously move electrons, and, for example, is preferable to include at least one selected from the group consisting of carbon nanotubes, graphene, metal nanoparticles, metal nanoparticles, metal nanowires, and nanofibers.

Meanwhile, the conductive material may be included in an amount of 0.01 wt % to 1 wt %, preferably 0.03 wt % to 0.7 wt %, based on the total weight of the hydrogel.

Here, when the conductive material is included in less than 0.01 wt %, the content in water or hydrogel is insignificant and movement of electrons is difficult, and therefore, it is difficult to exhibit sufficient electrical conductivity. When the conductive material is included in excess of 1 wt %, a trap phenomenon that reduces dispersibility and bonding properties of the composition for electrodes may occur, and thus electron transfer efficiency may be reduced.

The plurality of glass beads 113a may be dispersedly disposed in the first hydrogel layer 113, and a length of each of the glass beads 113a is in a range of the thickness T1 of the first hydrogel layer 113, and preferably is 8 μm to 12 μm. Meanwhile, the glass beads 113a may be selected from the group consisting of glass fibers, glass flakes, flat glass fibers, glass beads, and combinations thereof.

The plurality of glass beads 113a may prevent the transparency from being lowered by the algal cells in the first hydrogel layer 113 and may refract incident light due to a difference in refractive index of an interface to increase path through which light propagates in the first hydrogel layer 113, thereby increasing photosynthetic efficiency of the algal cells.

Even when the first hydrogel layer 113 gradually becomes opaque by the algal cells, an area in which the glass beads 113a are dispersed may improve transparency, and the light incident through the glass beads 113a may be refracted and reflected to increase the time maintained in the first hydrogel layer 113

Meanwhile, referring to FIG. 2, the glass bead 113a according to the inventive concept is shown in a rectangular columnar shape, but this is merely illustrated for convenience of description, and the glass bead 113a may be formed in various shapes, such as three-dimensionally spherical, elliptical, and polygonal columnar, and the inventive concept is not limited to the shape of the glass bead 113a.

Meanwhile, the longest length of the glass bead 113a is preferably in the range of the thickness T1 of the first hydrogel layer 113, which is 8 μm to 12 μm. That is, the longest length of the glass bead 113a may be similar to or equal to the thickness T1 of the first hydrogel layer 113.

Meanwhile, when a certain glass bead 113a is disposed to have the longest length in a thickness direction of the first hydrogel layer 113, the light incident from a top to the first hydrogel layer 113 may be directly incident on the certain glass bead 113a to be refracted in the glass bead 113am thereby being incident into an interior of the first hydrogel layer 113.

The plurality of glass beads 113a may be included in an amount of 0.1 wt % to 5 wt % based on the total weight of the hydrogel of the first hydrogel layer.

Here, when the glass bead 113a is less than 0.1 wt % relative to the total weight of the hydrogel, it is not possible to prevent the decrease in transparency and strength of the first hydrogel layer 113. When the glass bead 113a exceeds 5 wt % relative to the total weight of the hydrogel, the glass beads 113a may be included more than necessary, thereby decreasing photosynthetic efficiency of the algal cells.

Meanwhile, the first hydrogel layer 113 may be formed by any one coating method of bar coating, knife coating, and slot coating.

Here, when the glass beads 113a are included in the first hydrogel layer 113, it is preferable to apply a bar coating in which at least one glass bead 113a functions as a column.

In the disposing of the Nafion™ layer of S30, the Nafion™ layer 114 is disposed on the first hydrogel layer 113. The Nafion™ layer 114 is an ion conductive polymer electrolyte membrane, and serves to transfer hydrogen ions between the electrodes.

In the disposing of the second hydrogel layer of S40, the second hydrogel layer 115 is disposed on the Nafion™ layer 114.

When the hydrogen ions generated by the algal cells in the first hydrogel layer 113 diffuse through the Nafion™ layer 114, the second hydrogel layer may serve to collect the hydrogen ions and the conductive material may be dispersed.

The conductive material may be included in an amount of 0.01 wt % to 1 wt %, preferably 0.03 wt % to 0.7 wt %, based on the total weight of the hydrogel.

Here, when the conductive material is included in less than 0.01 wt %, the content in water or hydrogel is insignificant and movement of electrons is difficult, and therefore, it is difficult to exhibit sufficient electrical conductivity. When the conductive material is included in excess of 1 wt a trap phenomenon that reduces dispersibility and bonding properties of the composition for electrodes may occur, and thus electron transfer efficiency may be reduced.

In the disposing of the second transparent electrode of S50, the second transparent electrode 116 is disposed on the second hydrogel layer 115.

The second transparent electrode 116 may be a graphene electrode or an electrode including a graphene layer. The graphene layer itself may serve as an electrode or the second transparent electrode 116 including the graphene layer may be used by coating the surface of the second transparent electrode 116 with graphene.

Meanwhile, as described above, an electrode that is capable of being applied transparently and is not transparent may be applied as the transparent electrode. Pt or Au which is formed as a thin film withing 4 nm through vacuum deposition to secure transparency may be used as the transparent electrode. These materials are electrochemically stable materials, and in particular, Pt is a very electrochemically stable material, and therefore Pt or Au may be a preferable application example.

Graphene has a large mechanical strength, a large surface area, and excellent electrical conductivity as well as chemical stability, and thus, may be used as a medium for effectively transferring the hydrogen ions to the electrode.

Then, in the disposing the protective layer of S60, the second protective layer 117 may be disposed on the second transparent electrode 116, and thus the transparent microbial energy device 100 may be prevented from external impact.

EXAMPLE

1) Preparation of First Hydrogel Layer

Glass beads were dispersed in an amount of 0.1 wt % to 5 wt % with respect to the total weight of the hydrogel (polyethylene (glycol) Diacrylate, PEGDA, Sigma-Aldrich purchased). In addition, a conductive material (carbon nanotube) was dispersed at 0.01 wt % to 1 wt % with respect to the total weight of the hydrogel. Synechococcus cyanobacteria cells were grown in a culture medium of Blue Green Medium (BG11) for about a month, and then irradiated with a UV lamp three times to harden.

A first hydrogel layer was disposed as a single cell layer on the first transparent electrode through bar coating.

2) Preparation of Nafion™

Nafion™ 117 was prepared in a form of a thin layer, and laminated on a second hydrogel layer.

3) Preparation of Second Hydrogel Layer

Polyethylene (glycol) Diacrylate (PEGDA, purchased from Sigma Aldrich) was dissolved in distilled water at 1 wt % to 10 wt % to make a PEGDA solution.

After the conductive material (carbon nanotube) was dispersed at 0.01 wt % to 1 wt % with respect to the total weight of the hydrogel (polyethylene (glycol) Diacrylate, PEGDA, purchased from Sigma Aldrich), it is applied on Nafion™.

4) Assembly of Device

The first protective layer, the first transparent electrode, the first hydrogel layer, the Nafion™ layer, the second hydrogel layer, the second transparent electrode, and the second protective layer were sequentially disposed to form a transparent microbial energy device.

The transparent microbial energy device and a method of manufacturing the same according to embodiments of the inventive concept may efficiently capture hydrogen generated from the microorganisms using potassium ferricyanide, and may secure transparency by thinly coating the hydrogel layer containing algal cells to the thickness of the single cell layer.

The above detailed description is illustrative of the inventive concept. In addition, the above description shows and describes preferred embodiments of the inventive concept, and the inventive concept can be used in various other combinations, modifications, and environments. That is, changes or modifications are possible within the scope of the concept of the inventive concept disclosed herein, the scope equivalent to the written disclosure, and/or within the scope of skill or knowledge in the art. The written embodiment describes the best state for implementing the technical idea of the inventive concept, and various changes required in the specific application field and use of the inventive concept are possible. Accordingly, the detailed description of the inventive concept is not intended to limit the inventive concept to the disclosed embodiments. Also, the appended claims should be construed as including other embodiments.

What is claimed is:

1. A transparent microbial energy device comprising:
a first transparent electrode;
a first hydrogel layer disposed on the first transparent electrode and including algal cells;
an ion conductive polymer electrolyte membrane disposed on the first hydrogel layer;
a second hydrogel layer disposed on the ion conductive polymer electrolyte membrane and including potassium ferricyanide; and
a second transparent electrode disposed on the second hydrogel layer.

2. The transparent microbial energy device of claim 1, wherein the first hydrogel layer has a single cell layer structure and has a thickness of 8 to 12 μm.

3. The transparent microbial energy device of claim 2, wherein the first hydrogel layer includes a plurality of dispersed glass beads and a conductive material.

4. The transparent microbial energy device of claim 3, wherein the glass beads are included at 0.1 wt % to 5 wt % with respect to the total weight of hydrogel of the first hydrogel layer.

5. The transparent microbial energy device of claim 4, wherein the glass bead has a length of 8 to 12 μm.

6. The transparent microbial energy device of claim 1, wherein the second transparent electrode further includes a graphene monolayer.

* * * * *